United States Patent [19]
Babunovic et al.

[11] 4,108,762
[45] Aug. 22, 1978

[54] TRANSPARENT CONTAINER INSPECTION APPARATUS

[75] Inventors: Momir Babunovic, Des Peres; James R. Gender, Kirkwood; Siamac Faani, Ferguson; Mihai A. Bulboaca, Lemay, all of Mo.

[73] Assignee: Barry-Wehmiller Company, St. Louis, Mo.

[21] Appl. No.: 774,739

[22] Filed: Mar. 7, 1977

Related U.S. Application Data

[63] Continuation of Ser. No. 615,562, Sep. 22, 1975, abandoned.

[51] Int. Cl.² ............................................. B07C 5/342
[52] U.S. Cl. .............................. 209/111.7 T; 209/73; 209/74 R; 250/223 B; 356/240; 198/377; 198/441
[58] Field of Search ................ 209/73, 74 R, 111.7 R, 209/111.7 T; 250/223 B; 356/163, 240; 198/344, 366, 370, 375, 440, 441, 576, 611, 678, 680, 645, 653, 377

[56] References Cited

U.S. PATENT DOCUMENTS

| | | |
|---|---|---|
| 2,112,621 | 3/1938 | Henszey et al. ............... 209/111.9 X |
| 2,213,774 | 9/1940 | Taylor ............................ 198/653 X |
| 2,682,802 | 7/1954 | Fedorchak et al. ......... 209/111.7 TX |
| 3,382,974 | 5/1968 | Mayeux ................................... 209/73 |
| 3,517,794 | 6/1970 | Babunovic ........................... 198/440 |
| 3,606,013 | 9/1971 | Wideman .......................... 198/370 X |
| 3,770,969 | 11/1973 | Ansevin et al. ................... 250/223 B |
| 3,791,741 | 2/1974 | Brenholdt ..................... 250/223 B X |
| 3,932,042 | 1/1976 | Faani et al. .......................... 356/240 |

Primary Examiner—Joseph J. Rolla
Attorney, Agent, or Firm—Gravely, Lieder & Woodruff

[57] ABSTRACT

Apparatus for inspecting either empty or filled transparent containers for foreign matter in which the containers are moved through spaced apart inspection stations to present different sides thereof to high intensity pulsed light sources which casts the illuminated image beams along paths which intersect at a beam directing member operable to align and direct the respective beams into an electronic scanning device, and in which apparatus the containers at the respective inspection stations are not necessarily the same containers so that the inspection at the stations occurs in a predetermined sequence.

13 Claims, 23 Drawing Figures

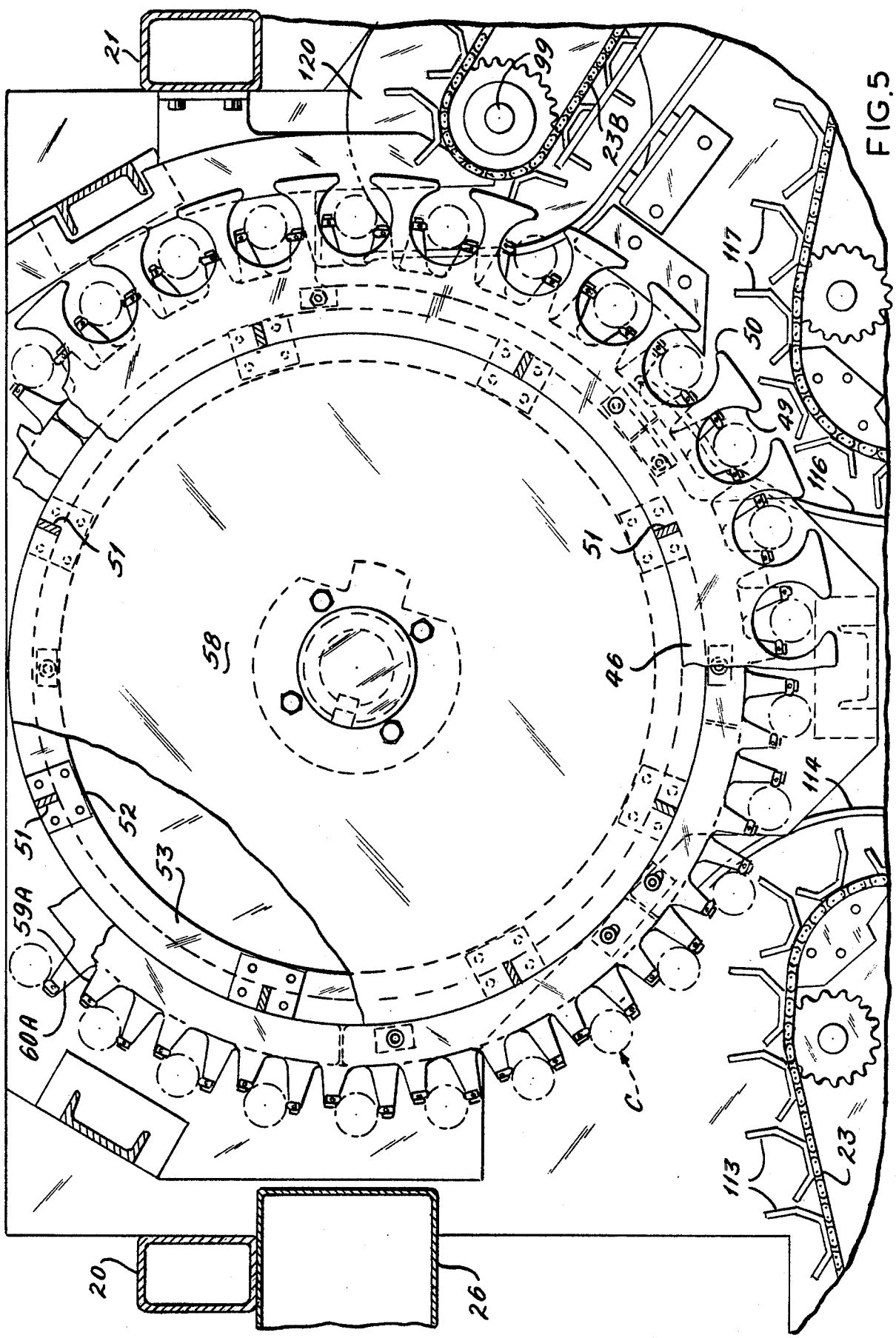

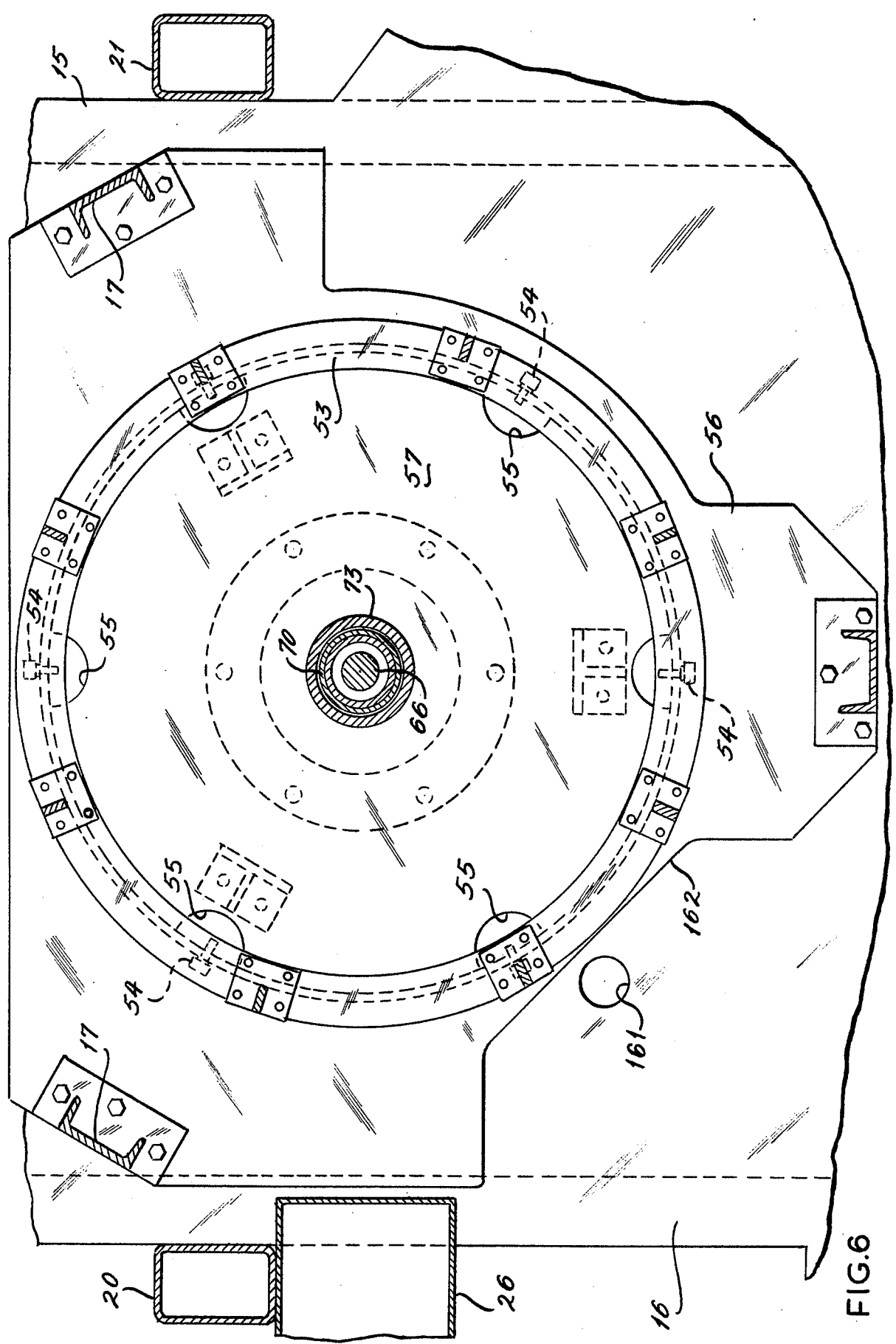

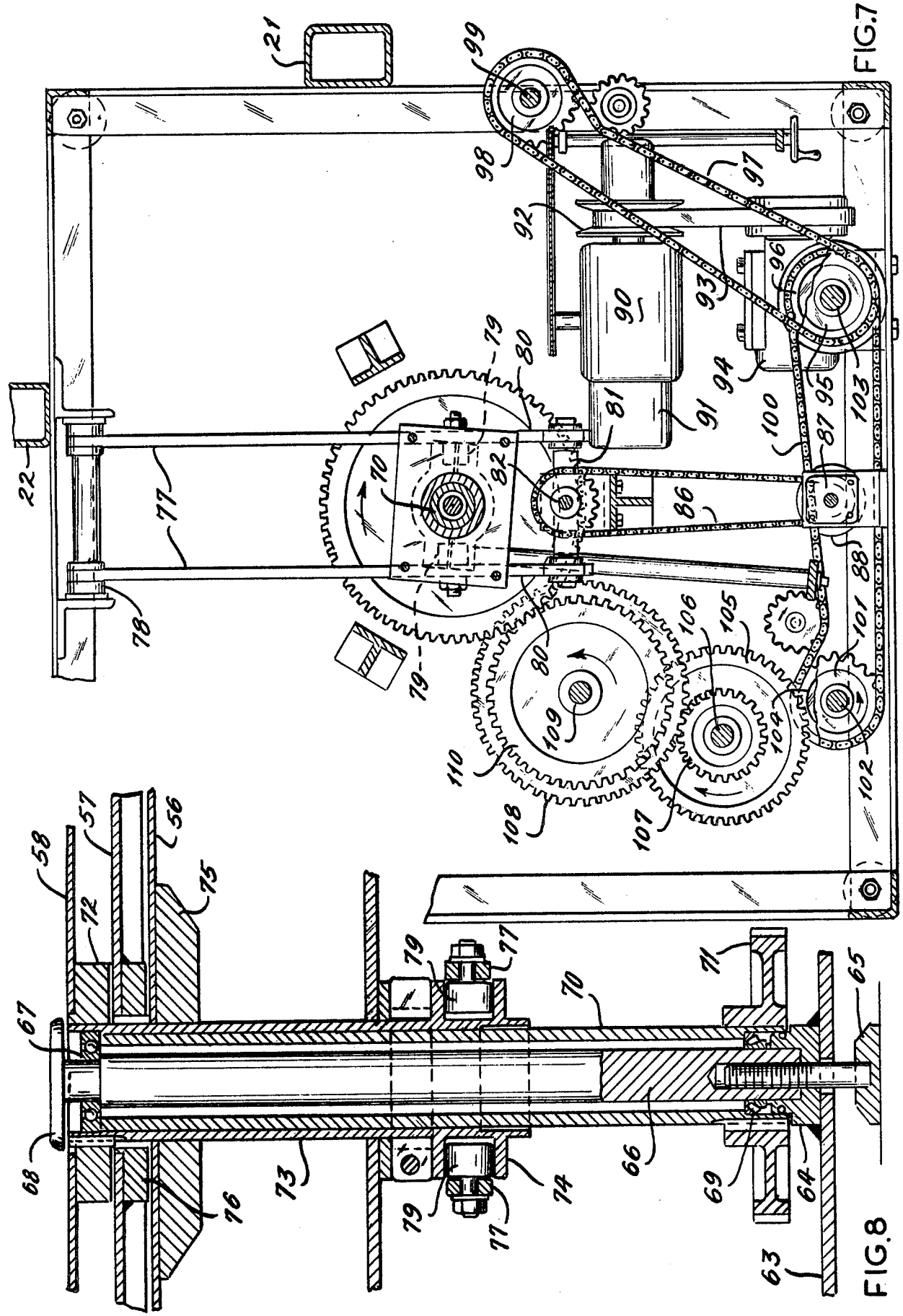

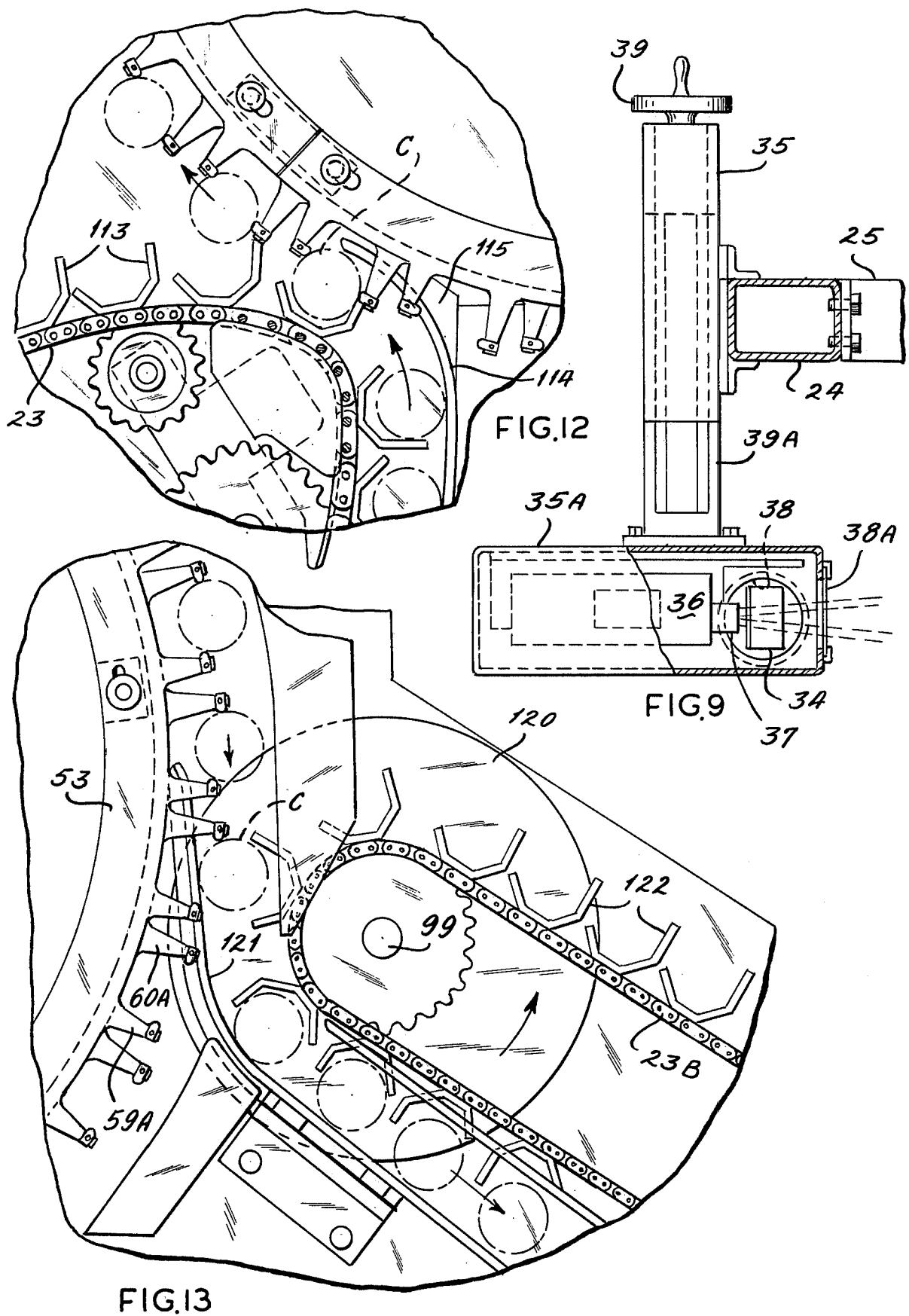

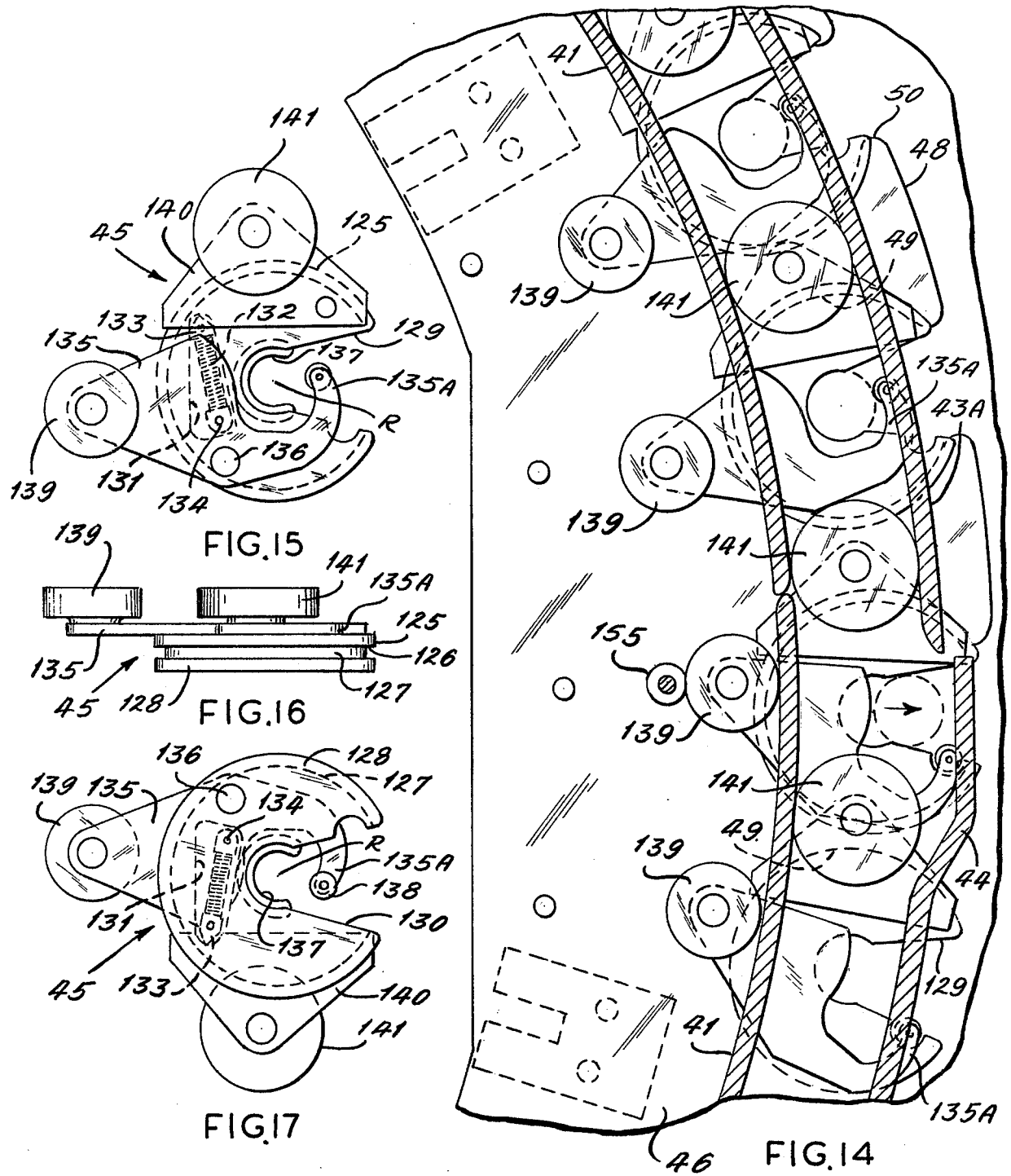

TRANSPARENT CONTAINER INSPECTION APPARATUS

This application is a continuation of application Ser. No. 615,562, filed Sept. 22, 1975, now abandoned.

BACKGROUND OF THE INVENTION

Containers used to market beverages require great care in presenting the same to the fillers to assure integrity of the structure and freedom from contaminating objects and substances. This is especially true when it comes to the use of returnable container which have undergone hard usage and which may have been used to catch waste substances, smoking stubs and ashes, and other objects, some of which are difficult to remove and some are located in the container in areas hard to inspect.

The market for beverage containers is immense and requires much more rapid inspection to develop the volume of containers needed to meet the demand and keep the filler equipment fully supplied. Consequently high speed apparatus is called for and equally high speed inspection devices are needed. To meet this challenge of large capacity inspection, the light transparent containers are exposed to a diffused light source which is passed through the container to produce an illuminated image which, by means of a lens system, is analyzed by a television scanning system. A system of this character is able to process container images for foreign objects by scanning containers from different sides at approximately ninety degrees of rotatory displacement. While vast numbers of containers need to be inspected, the apparatus hereof remained free of bulk and space consuming size through a unique arrangement of turret means to move the containers successively through the inspection stations in a high speed flow and to carry out the inspection by a single inspection unit.

BRIEF SUMMARY OF THE INVENTION

This invention relates to apparatus for moving containers through a plurality of inspection stations and to a unique method for viewing the containers from different sides without continuously rotating the containers.

It is an important object of this invention to inspect light transparent containers which may be empty, may contain liquid at less than standard level, or may have foreign matter by moving the containers through successive light beams which illuminate the whole container from different sides so that different images are produced to be scanned by sensing means which is responsive to changes in the level of light due to the presence of foreign material or objects, whether inside or outside, as well as liquid at less than the standard level, or foreign objects in a filled container.

It is another object of this invention to employ apparatus having the characteristics of being able to produce illuminated images of containers from different angles to obtain full inspection, to develop the images by pulsed light segments operating alternately at spaced apart stations, to superpose illuminated images of the same container nonsequentially and from different sides so that the combination of the images constitutes a complete inspection, to project illuminated images along different paths and observe them individually by the same sensing means, to illuminate the entire container and electronically limit the field of inspection to the contour of the container which is not distorted by marginal aberrations, and to perform the inspection of each container while it is in motion by a detection process using a compact organization of light sources, optical system and single sensing means.

Rapid inspection of non-rotating transparent containers was achieved by passing a light through the container from different angles and processing the illuminated images to compare those images with a lighting condition which was known to be acceptable. The image processing was carried out with a suitable lens system on an electronic scanning screen. A container known to be free of foreign objects was first tested with placement of foreign objects in different locations inside the container and on optical analysis the objects on the main or central axis showed a true picture, but as the objects were moved laterally from the central axis the image intensity and shape changed and the deterioration in the quality of the images was more pronounced until the images disappeared when moved to a lateral position about 90° off the main axis of view. This procedure showed that to be able to successfully process a container illuminated image for foreign objects a minimum of two views at 90° to each other will be satisfactory. The challenge then was to simplify and condense the bulk of the inspection apparatus so there would result a commercially compact apparatus having great accuracy. The resulting apparatus embodies a unique system of container handling means associated with illuminating stations which cooperate with a single sensing means for detecting the presence of objectionable objects inside or outside or whether the container is empty or filled.

BRIEF DESCRIPTION OF THE DRAWINGS

The preferred embodiments of apparatus to achieve container inspection in the manner briefly outlined above are shown in the several views set forth in the accompanying drawings, wherein:

FIG. 3A is a detail at line 3A—3A in FIG. 1;

FIG. 5 is an enlarged and fragmentary plan view of the apparatus when seen along line 5—5 in FIG. 2;

FIG. 6 is a further enlarged and fragmentary plan view of the apparatus seen along line 6—6 in FIG. 2;

FIG. 7 is yet another enlarged and fragmentary plan view taken along line 7—7 in FIG. 2 to show the drive organization;

FIG. 8 is a fragmentary sectional view taken along line 8—8 in FIG. 2 showing portions of the operating means;

FIG. 9 is an enlarged and fragmentary side view, partly in section, of the sensing unit, as seen along line 9—9 in FIG. 1;

FIG. 12 is an enlarged and fragmentary plan view of the container infeed portion seen in FIG. 1;

FIG. 13 is an enlarged and fragmentary plan view of the container reject portion seen in FIG. 1;

FIG. 14 is another greatly enlarged plan view of the container reject means;

FIGS. 15, 16 and 17 respectively are top plan, side elevation and bottom plan views of the container gripping device heretofore shown in the views of FIGS. 4 and 14;

DESCRIPTION OF THE EMBODIMENT

Figure 1:
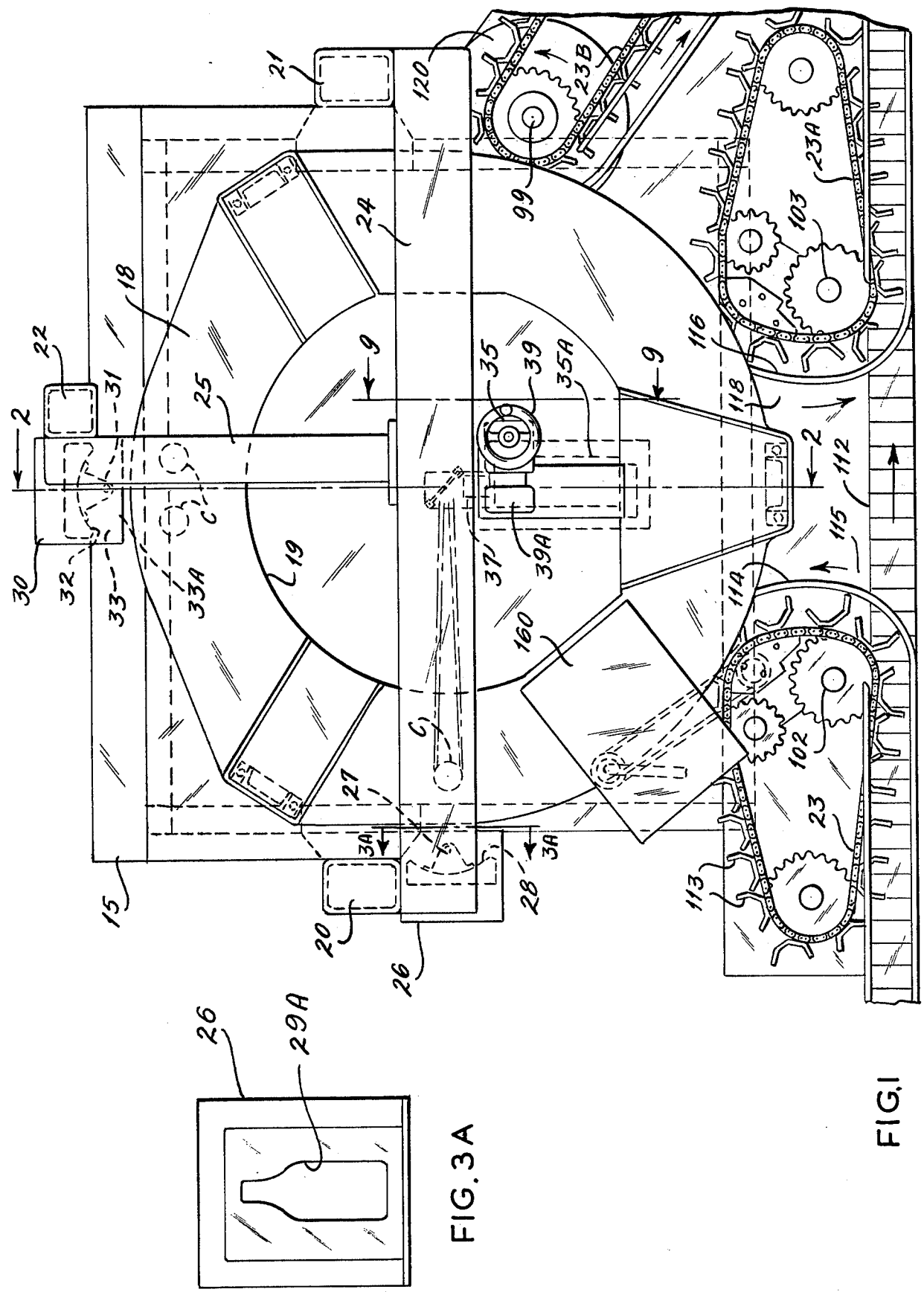
FIG. 1 is a general plan view of the inspection apparatus showing the conveyors arranged to feed containers for inspection, receive inspected and approved containers, and receive rejected containers.

The inspection of the whole container by a single image scanning means is accomplished by feeding the containers in spaced relation into peripheral pockets of a rotating turret head where they are engaged by gripper means at the necks so the container body is free on all sides. The turret head supports the grippers and orients the containers so they are gradually turned about the longitudinal axis to present different sides about 90° apart to inspection in conjunction with the energization of high intensity light pulses set off by the presence of the container at each inspection station.

The container spacing on the turret head is selected by the largest container diameter to be handled and the ability to produce a full illumination of the containers. The illuminated images produced by pulsed light sources are directed in a sequential relation to a beam directing device located adjacent the central axis of the turret so that these images may be individually focussed on a conventional television camera screen. The camera may be equipped with a commercial lens assembly which is generally a component supplied with the camera. It is important to direct the axis of the illuminated images at 90° to each other and have them intersect at the beam direction device so that the sequential pulsing of the different light sources will produce one image at a time at the beam directing device and not confuse the camera with superposed images. The operation of the light sources are in a flip-flop manner so that the illumination of one light source guarantees that the other light source will be off and prevent accidental pulsing of the light sources simultaneously. In an arrangement of the foregoing character the speed of response of the TV camera determines the speed at which the containers can be moved, and where two sequential inspections are to be made, the camera speed of response is twice the speed of container movement by the turret.

The present apparatus, as seen in top plan view, is partly contained in and operably mounted on a base housing 15 (FIGS. 1 and 2) having a top plate 16 (FIGS. 2 and 6) as will be noted presently, there is a top plate 18 spaced above the plate 16, and the plate has a central opening 19. The base housing 15 is a support for vertical posts 20 and 21 on opposite sides of the base, and a third vertical post 22 on a third side opposite the side of the base where the container feeding conveyor 23 and the discharge conveyor 23A are mounted. The posts 20 and 21 carry a cross beam 24 set in a horizontal position so as to cross over the top plate 18 above the central opening 19. A second horizontal beam 25 (FIG. 1) is secured at one end to the cross beam 24 and at the opposite end to the third post 22.

The left end (FIG. 1) of the cross beam 24 at the vertical post 20 supports a box 26 which houses a source of light which is a vertically elongated lamp 27 (FIG. 3) positioned to the inside of a focussing reflector 28, and the reflector 28 directs the light beam rightwardly through a diffusion plate 29 toward the center of the opening 19. A mask 29A with a container shaped aperture is positioned in front of the diffuser 29 to block unwanted light. The outer end of the second horizontal beam 25 (FIG. 1) and the vertical post 22 supports a second box 30 which houses a vertical elongated lamp 31 set to the inside of a focussing reflector 32, and the reflector 32 directs the light beam through a diffusion plate 33 and a mask 33A with a container shaped aperture placed over the diffuser inwardly toward the center of the opening 19 to intersect with the light beam from the reflector 28 at a beam splitter shown at 34 supported from underneath the cross beam 24 (FIG. 1). FIG. 9 in conjunction with FIG. 1 shows a post 35 carried by the cross beam 24 and supporting at its lower end a housing 35A for a television camera 36 which has its usual lens barrel assembly 37 positioned behind the beam splitter 34 aligned with windows 38 and 38A at the front of the housing 35A. The camera 36 is part of a scanning system (FIG. 21) for inspecting containers as they are passed across the light beams projected generally radially inwardly from the lamp boxes 26 and 30 to be handled by the beam splitter 34 which has substantially equal reflectance and transmittance. The light beam from box 26 is directed through a suitable filter 38 and reflected by the beam splitter 34 into camera 36 and the light beam from box 30 is directed through a suitable filter 38A and then transmitted through the splitter 34 to camera 36. As the vertical dimensions of the containers may change from run to run, the camera housing 35A can be vertically adjusted by rotating the elevating wheel 39 at the top of post 35, and this moves the slide 39A attached to housing 35A.

Figure 2:
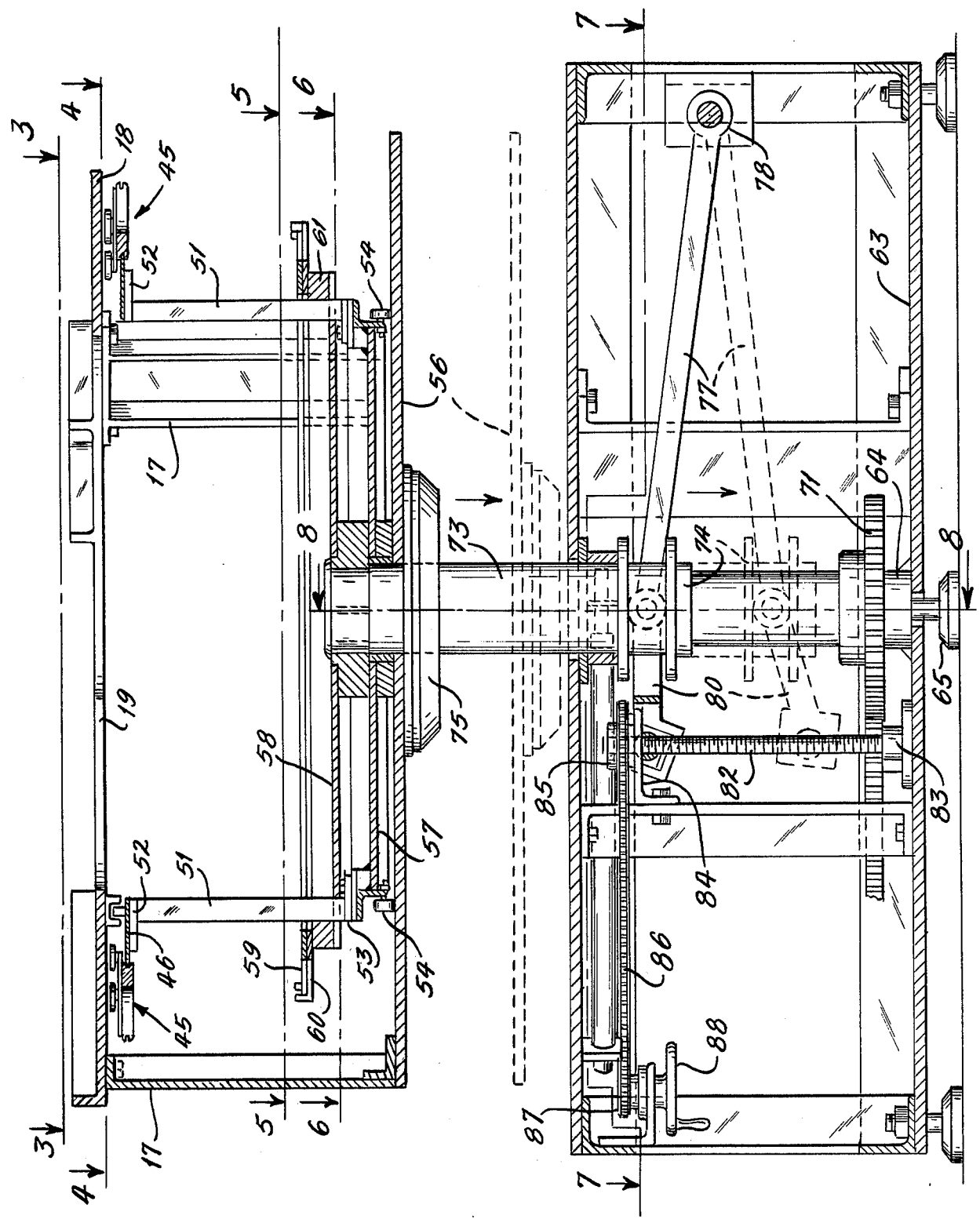
FIG. 2 is sectional elevation taken along line 2—2 of FIG. 1.
Figure 3:
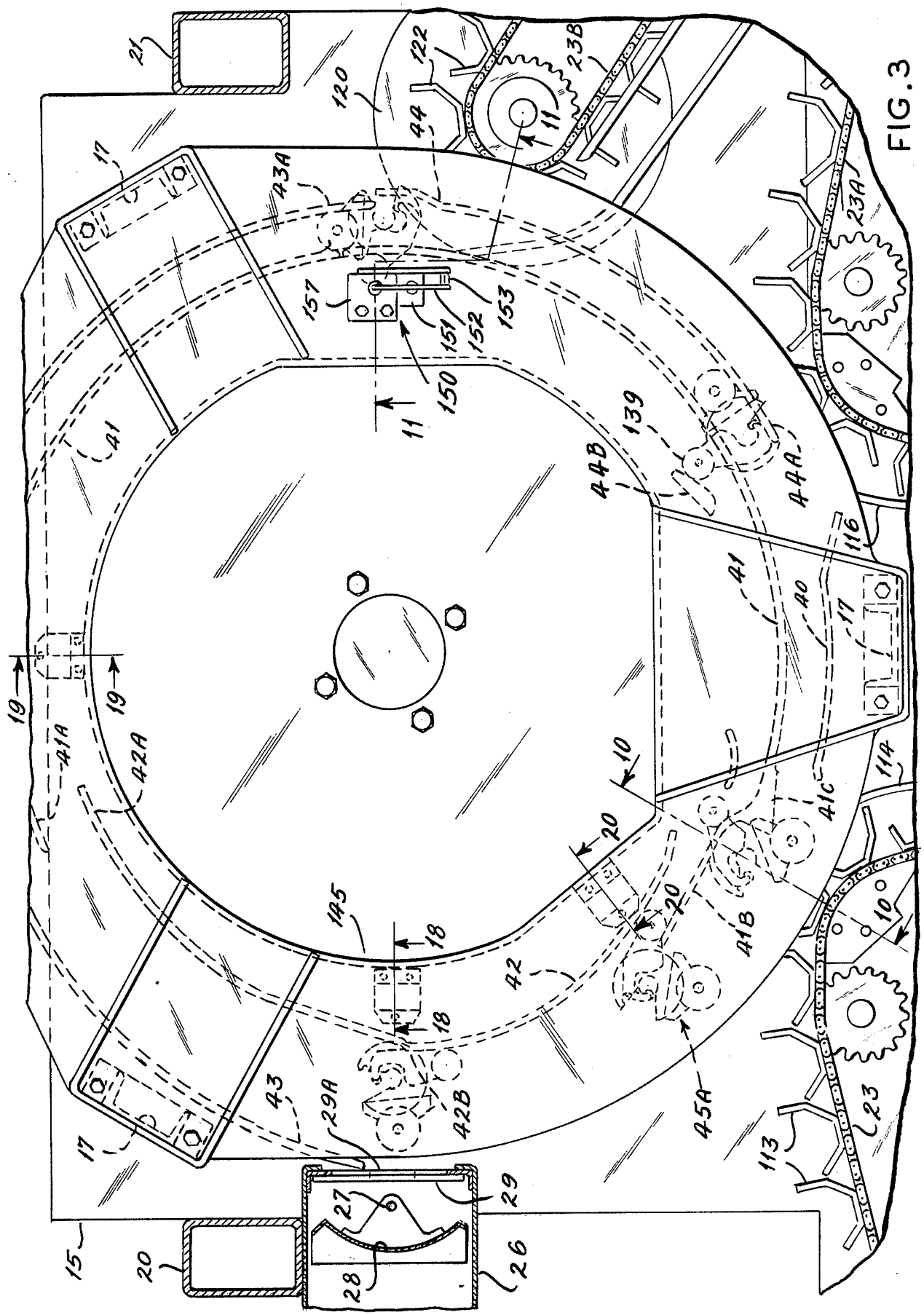
FIG. 3 is an enlarged and fragmentary plan view of the apparatus when seen along line 3—3 in FIG. 2.

FIG. 3 is an enlarged plan view at the level indicated in FIG. 2 of the top plate 18 supported on three channel shaped posts 17 carried by a vertically adjustable plate 56 (FIG. 2) to be referred to presently. The under surface of plate 18 supports a series of cooperating cam elements which are shown in dotted outline in FIG. 3 and in full line in FIG. 4. These cam elements are seen at 40 and 41 with element 41 extending more than 180° counterclockwise to a beginning end 41A and terminating at end 41B after passing an enlargement portion 41C. Where cam element 41B ends a cam element 42 begins with an overlap and extends clockwise to the ending 42A which slightly overlaps the beginning end 41A of cam element 41. Another cam element begins at 43 adjacent the lamp box 26 and continues clockwise to its ending 43A just beyond the vertical post 21 at the opposite side approximately 180° away. A still further cam element 44 begins where cam element 43A ends and extends clockwise to ending 44A.

Figure 4:
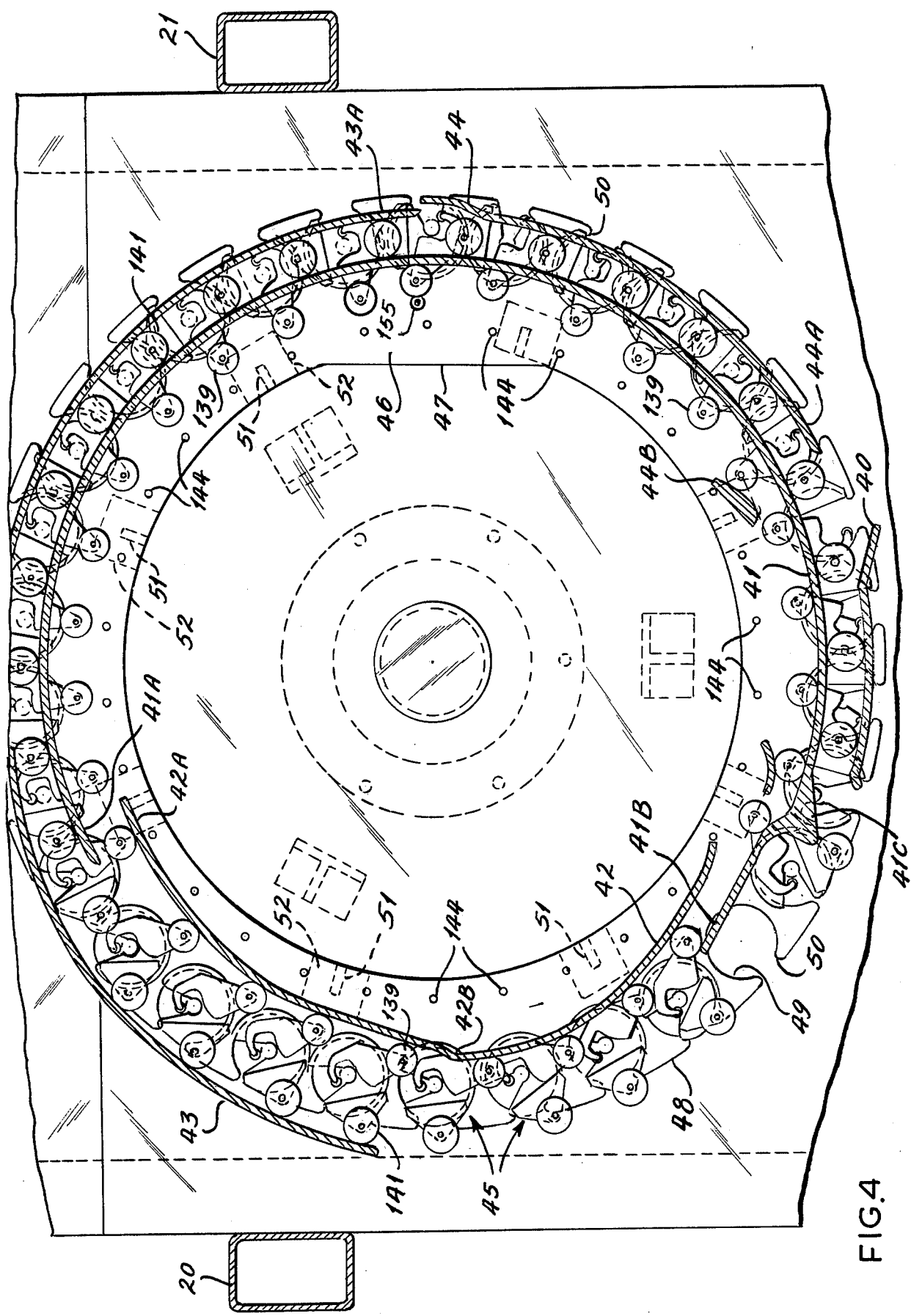
FIG. 4 is an enlarged and fragmentary plan view of the apparatus when seen along line 4—4 in FIG. 2.
Figure 10:
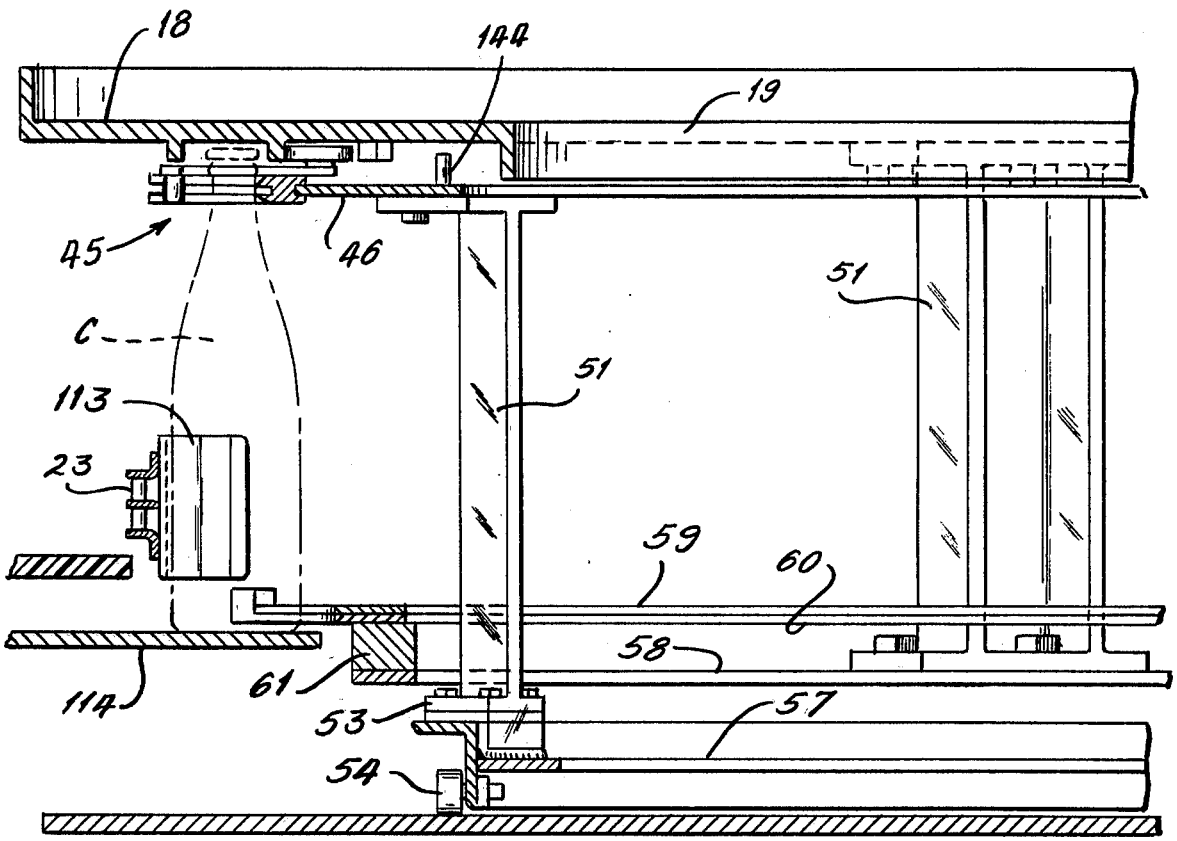
FIG. 10 is a fragmentary sectional elevational view of the container engaging and gripping means at the infeed side of the apparatus, the view being taken along line 10—10 in FIG. 4.

These several cam elements are attached to and held in fixed positions on the under surface of the plate 18 so that they may manipulate a series of container neck grippers 45, the details of which will be set forth in connection with FIGS. 15, 16 and 17. FIG. 4 discloses a ring plate 46 having a center opening 47 and a periphery 48 interrupted by a series of circular recesses 49 which open at notches 50 in the periphery 48. In the example shown there are 30 such notches opening to the recesses, and each associated recess 49 receives a gripper 45 which may turn or rotate within the recess, as dictated by the cam elements for the respective positions of circular travel of the grippers 45 as the plate 46 rotates.

The plate 46 is supported just below the top plate 18 by a plurality of vertical posts 51 which are eight in number and are connected to the plate by attachment brackets 52. These posts 51 are mounted upon a supporting ring 53 (FIGS. 2 and 6), and the ring 53 carries a plurality of support rollers 54 which roll on a non-rotatable but elevationally adjustable plate 56. Access to the respective rollers is lead through the openings 55 (FIG. 6). The supporting ring 53 is attached to the rotating plate 57 (FIGS. 2 and 6). As seen in FIGS. 2 and 5, plate 57 is positioned just below an upper plate 58, and the latter carries several pairs of fingered segments 59 and 60 about its periphery, and these segments are operatively supported on pads 61. The fingers 59A on the upper segments are shorter than the fingers 60A on the lower segments, and the outer tips of all of these fingers are provided with pads for contacting the side of the containers at the bottoms thereof.

Plate 58 is slotted radially inwardly at the necessary places to receive the vertical posts 51, and by this engagement the posts 51 drive the plate 58 on which the fingered segments 59 and 60 are carried. The segments 59 and 60 are relatively angularly adjustable to vary the spacing S (FIG. 5) between the fingers 59A and 60A to suit the diameter of the containers C. The structure above described is rotated to carry the flow of containers C from the infeed conveyor 23 to the discharge conveyor 23A, or to a reject conveyor 23B. It should be understood that the adjustable plate 56 does not rotate, but can be moved vertically for the purpose of locating the top plate 18 and the gripper carrying ring plate 46 at the proper elevation to place the grippers 45 in position to engage the neck of the containers just below the crown reinforcing ring. This vertical adjustment allows the posts 51 to slide through the radial slots in the rotating plate 58, but does not affect the fixed elevation of the fingered segments 59 and 60, as well as the supporting plate 58. As a result, the fingers 59A and 60A have a fixed elevation and the overhead grippers 45 are adjustable toward and away from those fingers to accommodate the length of the containers. The setting of these components seen in FIG. 2 is for the tallest containers.

The drive for the components which must rotate is seen in FIGS. 2, 7 and 8. The housing 15 has a floor plate 63 which supports a bottom thrust pad 64 set over an adjustable foot pad 65 for holding the floor 63 from sagging under the weight of the components and complement of containers above. The thrust pad 64 is engaged by the bottom end of a fixed spindle 66 (FIG. 8) which extends vertically to a top bearing 67 under the cap 68. The top bearing 67 and a cooperating bottom bearing 69 adjacent the thrust pad 64 carry a driven torque tube 70 surrounding the spindle 66. A drive gear 71 is suitably keyed to the lower end of torque tube 70 so that the tube 70 rotates but does not move vertically. The upper end of the torque tube 70 carries a hub 72 which supports the plate 58 at the desired elevation. The torque tube 70 provides the working bearing surface for a sleeve 73 formed with a yoke 74 at its lower end and with an enlarged support disc 75 at its upper end on which the plate 56 is carried. The upper central area of plate 56 supports a spacer block 76 to carry the central area of plate 57 and keep it level with the rollers 55 spaced around the periphery.

The vertical adjustment of the sleeve 73 is accomplished by a pair of radius arms 77 suitably pivotally mounted in a fixed bearing 78 on the side of the housing 15 adjacent post 22. The inner ends of the arms 77 are provided with rollers 79 (FIGS. 7 and 8) which ride in the yoke 74. The arms 77 have extensions 80 beyond the rollers 79 to carry a suitable clevis device 81 operatively engaged on a vertically directed screw shaft 82 (FIG. 2). The shaft 82 is supported by a bottom foot 83 and by an upper bracket 84 which also supports a drive sprocket 85 fast on the shaft 82. The sprocket 85 is rotated by a suitable chain 86 engaged on a sprocket 87 connected in a suitable manner to the hand wheel 88 (FIG. 2). Rotation of the hand wheel 88 drives the screw shaft 82 and causes the clevis device to move up or down, as desired, the result of which is to swing the radius arms 77 about the axis of the support 78 (FIG. 2) between the raised (full line) position and the lowered (dotted line position). This movement effects the position of the plate 56 between the corresponding full line and dotted line positions. While the sleeve 73 is adjustable vertically and does not rotate, the torque tube 70 on which it slides does rotate.

The drive arrangement for rotating the vertical torque tube 70, and also for driving the infeed conveyor 23, the discharge conveyor 23A and the reject conveyor 23B is best seen in FIG. 7 which is a fragmentary plan view of the power train beginning at the electric motor 90 having a brake unit 91 thereon and a variable speed output pulley 92. The pulley 92 is connected by belt 93 to speed reducer gear box 94 having a pair of side-by-side sprockets 95 and 96. The outside sprocket 95 is connected by chain 97 to sprocket 98 on the vertical shaft 99 associated with the reject conveyor 23B (FIG. 1). The inside sprocket 96 is connected by chain 100 to a sprocket 101 on the vertical shaft 102 for the infeed conveyor 23. The sprockets 95 and 96 are mounted on vertical shaft 103 for the discharge conveyor 23A.

The drive to shaft 102 (FIG. 7) also rotates a gear 104 fixed on this shaft, and gear 104 meshes with a gear 105 on a shaft 106, and shaft 106 drives gear 107. The gear 107 meshes with gear 108 on shaft 109, and this drives gear 110 and eventually the gear 71 on the torque tube 70 (FIG. 8). This gear train associated with motor 90 coordinates the operation of the container infeed, discharge and reject conveyors in proper relation to the rotation of the container neck grippers 45 and the fingered segments 59 and 60 which steadies the bottom of the containers. Rotation of hand wheel 88 effects the vertical elevation of the grippers 45.

There is shown in FIG. 1 a container conveyor 112 which provides a flat top surface for bringing containers into the orbit of the infeed conveyor 23, and the conveyor 112 continues on past the orbit of the discharge conveyor 23A. A conveyor of the type 112 common to both conveyors 23 and 23A is not always necessary or desirable and is only shown to illustrate one type of installation. As containers are segregated by the moving pockets 113 they are confined by the fixed curved rail 114 to pass over a dead plate 115 (FIG. 12) until the bottom of the containers are pushed into the space formed between a short finger 59A in front and a longer finger 60A which follows up. As can be seen in FIG. 3 the arrival of the container at the paired fingers 59A and 60A is timed to agree with the arrival of an open neck gripper 45. After a container has travelled the circuit of the apparatus, and is found to be acceptable, it is brought into the orbit of the discharge conveyor 23A which has a fixed guide rail 116 (FIGS. 1, 3 and 5) which extends into the path of container travel and guides them into the respective pockets 117 on the conveyor 23A. The grippers 45 are opened at the proper time and release the containers onto a dead plate 118 at the moment when the longer trailing edge of the conveyor pocket is able to engage the container and confine it against the guide rail 116.

Should a container be found objectionable it will be rejected onto a rotating table 120 (FIGS. 1, 3, 5, 11 and 13) which is set below the elevation of the fingered segments 59 and 60 (FIG. 11) a suitable distance to allow the crown ring and mouth of the container to drop and clear the gripper 45. The gripper 45 is opened at the proper time so that as the container reaches the reject drop off point it will be within the reach of the guide rail 121 and ready to be engaged by the pocket 122 on the reject conveyor 23B.

Attention will be directed to FIGS. 15, 16 and 17 for an understanding of the container gripper 45. The gripper has a body disc 125 formed with a ledge 126 and a circular body recessed portion 127 which is sized to have a working fit in the circular recesses 49 (FIG. 14) formed in the periphery of the ring plate 46 which carries all of the grippers. This body 125 is seated on top of plate 46 so the recessed portion 127 extends through the recess 49 slightly more than the thickness of the plate 46. A retainer plate 128 is secured to the recessed portion 127 to hold the body in the recess so it is free to rotate. Both body 125 and retainer 128 have a slot 129 and 130 respectively cut therein to extend in aligned relation through the center of rotation R. The body 125 is formed with an aperture 131 to receive a toggle spring 132 having one end engaged in an abutment element 133 seated against one end of the aperture 131. The opposite end of the toggle spring 132 is anchored on a pin 134 which is mounted in a jaw plate 135. The jaw plate 135 is pivotally mounted on the top surface of the body 125 (FIGS. 15 and 16) by a pivot pin 136 such that the pin 134 for the toggle spring 132 projects into the aperture 131. It is understood that the pivot 136 and the abutment element 133 are aligned with the aperture 131 so that the anchor pin 134 for the toggle spring 132 may move to one side or the other of a line between the abutment 133 and the axis of the pivot 136 so that the jaw plate 135 will be pressed by the spring into either one of two positions. The jaw plate 135 has its capture hook 135A projecting across the slots 129-130 to close over the neck portion of a container and suspend it substantially at the center of rotation R in the slots. The slot 129 is suitably recessed to receive a rubber pad 137 which extends around in the slot and cushions the container neck when the toggle spring 132 snaps the jaw capture hook 135A across the neck. The extremity of the hook 135A is provided with a lip pad 138 to complement the cushion 137. The movable jaw plate 135 carries a roller 139 at its outer end, and the body 125 carries a plate 140 fixed in position and adapted to support a second roller 141 spaced from the movable roller 139. Each gripper 45 is mounted on the plate 46 by inserting the body 125 into the circular recess 49 and then attaching the retainer plate 128 after the toggle spring 132 has been installed. The view of FIG. 15 shows the gripper 45 in its closed position, but in the view of FIG. 14 the gripper 45 at the lower end of that view is shown in its container release position with the roller 139 swung to a position closer to the roller 141, and this results in the jaw plate projecting a surface 135B into the recess R to push the container through the slots 129–130.

OPERATION OF THE APPARATUS

The apparatus above described is adjusted for the body diameter and height of the containers to be inspected by relatively angularly sliding the segments 59 and 60 until the spacing between the respective fingers 59A and 60A is correct. Electrical power may now be supplied to the various inspection devices and to the motor 90 which initiates proper coordinated operation of the reject conveyor shaft 99, the discharge conveyor shaft 103, the infeed conveyor shaft 102 and the torque tube 70 (all shown in FIGS. 7 and 8).

Figure 18:
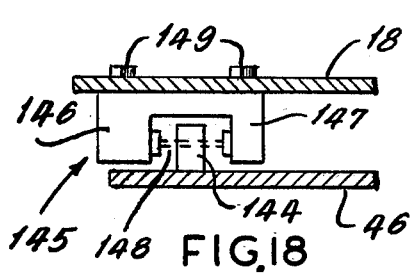
FIGS. 18, 19 and 20 are respectively fragmentary sectional views of electrical sensing devices for the container inspection stations; the views being taken at lines 18—18. 19—19 and 20—20 in FIG. 3.
Figure 19:
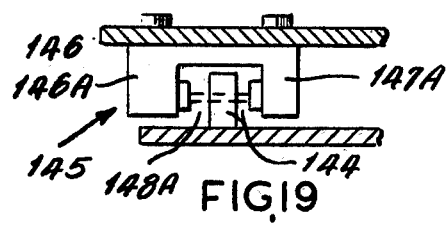
Figure 20:
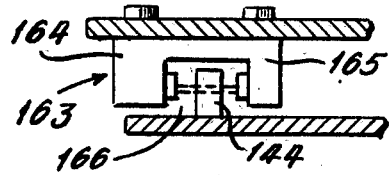

Rotation of shaft 102 begins feeding containers into the turret head, if containers are available. It also rotates the torque tube 70 which (FIG. 2) initiates the rotation of the plate 57, and through posts 51 rotates the segments 59 and 60. The posts 51 transmit movement to the plate 46 and all of the grippers 45 thereon. Plate 46 also carries upwardly projecting position sensing pins 144, one for each grippers, and these pins are successively moved through appropriate electrical sensing devices. One of the devices 145 (FIGS. 3 and 18) aligned with the light box 26 is fixed to and depends from the top plate 18, and is in the form of a housing carrying a source of light in a housing portion 146 and a photosensitive receiver in a housing portion 147. The housing portion 147 is spaced from the portion 146 to form a gap 148 for the passage of the sensing pins 144. The device 145 is adjustable and is secured by threaded means 149. Similarly, a second device 145A is aligned with the light box 30 (FIGS. 1, 3 and 19). This device 145A has a housing with a depending portion 146A spaced from portion 147A to form a gap 148A through which sensing pins 144 pass to break the light beam projecting from portion 146 toward the receiver in portion 147A. The housing 145A is adjustable for allowing for proper location of the beam. These devices 145 and 145A are for the purpose of controlling the energization of the lamps 27 and 31 in the respective boxes 26 and 30 (FIG. 1) in sequence and when a container has reached a position opposite lamp 27 and then opposite lamp 31. As will appear presently when a container reaches a position opposite lamp 27 a sensing pin 144 will intercept the light beam projected from housing 146 (FIG. 3) and the receiver will be triggered to energize the lamp 27. At this time there will be no container opposite lamp 31, but when the plate 46 rotates a distance equal to one-half the distance between two pins 144 another pin 144 will pass through the gap 148A in front of light source 146A and that will trigger the energization of the second lamp 31, and at that time a container (not necessarily the one opposite lamp 27) will be opposite that lamp.

As containers are fed by infeed conveyor 23 (FIGS. 1, 3 and 4) the grippers 45 will move at synchronous speed to arrive at the position of gripper 45A (FIG. 3) with its jaw 135A in the open position. This open position is obtained by the cam block 44B forcing the roller 139 to back up (due to the direction of rotation) toward the roller 141 by reason of the roller 141 being caged between the cams 41 and 44. Each gripper 45 is conditioned in this manner before it reaches the infeed conveyor 23, thereby presenting an open slots 129–130 to the incoming container neck. The receipt of the neck in the slots will coincide with the gripper 45A being manipulated by the cam enlargement 41C of cam 41 spreading the rollers 139 and 141 which causes the jaw 135 to pivot into the position where the portion 135A closes over the slots 129–130. The container is at this moment captured in the gripper 45A and is securely held in position with its body suspended from plate 46. All containers will be similarly secured.

Continued rotation of plate 46 will carry the suspended containers to the first side inspection station represented by the light source 27 in the light box 26. As noted above, when the container aligns with the lamp 27 the associated sensing pin 144 moves into the gap 148 in the sensing device 145 and through a circuit to be described will trigger lamp 27 to produce a high intensity flash of light. The light will illuminate the whole container body and project that image upon the beam splitter 34 (FIGS. 1 and 9) which will reflect it into the camera 36 for scanning for foreign objects. As a container leaves its alignment with lamp 27, a different container will move into alignment opposite the second side inspection station represented by the light source 31 in light box 30. At this time the associated sensing pin 144 will intercept the light source 146A in sensing device 145A (FIGS. 1, 3 and 19) and cause the lamp 31 to produce a high intensity flash of light to illuminate the whole container body. The illuminated image will be projected to the beam splitter 33 and will be transmitted through it into the camera 36.

It should be understood that the container reaching the second station at lamp 31 has travelled through the first station at lamp 27. In order to present a different side of the containers to lamp 31, the grippers 45 are manipulated to turn each container about 90° between stations one and two. The turning is accomplished by the fixed cam elements 42 seen in FIGS. 4 and 5 in the following manner. As a gripper 45 leaves the first station at light box 26 the inside cam element 42 is formed with a joggle 42B which sets the cam element inwardly a distance sufficient to establish a clearance at the roller 139 on the movable jaw plate 135. This clearance occurs simultaneously with the fixed roller 141 engaging the outside cam element 43. The cam element 43 is set on an inward spiral relative to the center of rotation of the plate 46 and since the fixed roller 141 trails the position of the container neck the clockwise rotation of plate 46 will cause the cam element 43 to push the roller 141 inward, thereby turning the container about its longitudinal axis in a counterclockwise direction as it is bodily carried in a clockwise direction. The cam element 43 will effect a container turn of about 90° by the time the gripper reaches the second station at light box 30.

During the approach of a gripper 45 to the second inspection station cam element 42A ends and the beginning end 41A of a cam element is reached. The outside cam 43 and inside cam 41 cooperate to retain the fixed roller 141 of the gripper and hold the gripper jaw plate roller 139 in a position such that it must follow a path which may cause it to engage an obstruction to its free movement when that obstruction is present. If the obstruction is not present to intercept the motion of the roller 139, it will continue on with the other roller 141 remaining trapped between the outside cam element 44 (FIG. 4) and the inside cam element 41. When the jaw plate roller 139 engages the fixed cam block 44B it will cause the jaw plate 135 to pivot to open the slot 129–130 by moving the roller 139 toward roller 141. At this time the container neck will be released to deposit the container on the supporting dead plate 118 (FIG. 1) within the reach of a pocket 117 on discharge conveyor 23A. This completes the travel of a gripper 45 from the infeed conveyor 23 where each container is engaged through the circuit of container flow to the release of each container at the discharge conveyor 23A.

Figure 11:
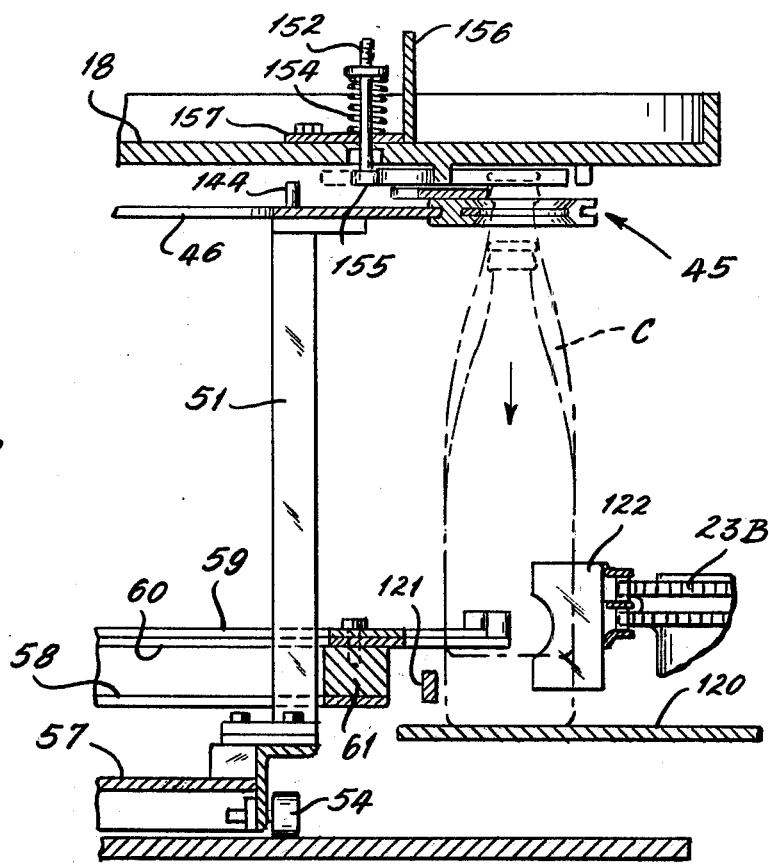
FIG. 11 is a fragmentary sectional elevational view of the container rejection station as seen along line 11—11 in FIG. 3.

If a container is sensed at either station denoted by light boxes 26 or 30 to be unacceptable, a circuit in the camera 36 connected with the solenoid (FIGS. 3, 11 and 14) of a reject device 150 will energize the solenoid 151 to move the lever 152 about its pivot 153, and against the lift of the spring 154, and project the plunger head 155 downwardly to form the obstruction to the movement of the jaw plate roller 139. This organization of parts is operatively carried by a panel 156 supported on a foot plate 157 attached to the top surface of the plate 18. The location of this reject device 150 (FIG. 3) is adjacent the transition between cam element end 43A and the beginning of cam element 44. The obstruction formed by projecting the plunger head 155 will move the roller 139 toward roller 141 and pivot the jaw plate 135 to open slots 129–130 for release of the rejected container onto the rotating table 120 (FIG. 11).

The foregoing description has set forth the arrangement of inspection stations at light boxes 26 and 30 where the whole side of a container suspended by the reinforcing element of its crown ring is illuminated and the image projected onto a beam splitter 34 which directs the image into a photosensitive scanner, such as a TV camera 36. The side of the container illuminated by lamp 31 is 90° displaced from the side illuminated by lamp 27 so that a complete scan of the interior and exterior is accomplished. The gradual turning of each container between the first and second stations is effected by the character of fixed cam elements and roller means on the grippers 45. The devices 145 and 145A, working in response to the travel of the sensing pins 144, control the time of energization of each lamp 27 and 31 so that when a container is in front of the box 26 for lamp 27, a pair of containers straddles the "in front" alignment at box 30 for lamp 31; and when a container is aligned with lamp 31, a pair of containers straddles the "in front" alignment at box 26 for lamp 27.

The foregoing apparatus is capable of having additional devices added to it for performing other character of container inspections. For example, if container bottom inspection is to be performed, it can be accomplished by mounting the inspection head 160 (FIG. 1) on the stationary top plate 18 adjacent the infeed conveyor 23. Such a device is disclosed in Wyman U.S. Pat. No. 3,191,773, granted June 29, 1965 and assigned to the present assignee of this application. The device of that Wyman patent, represented by the box 160 in FIG. 1 is incorporated herein by reference and the container inspection performed thereby is adopted for this apparatus with suitable connection to a central electrical circuit (FIG. 21) which will at the proper time relay the reject signal produced by the reject relay 82 of said U.S. Pat. No. 3,191,773 to the solenoid 151 of the present reject device 150 (FIGS. 11 and 14). Provision is made in the plate 16 of the present structure through an aperture 161 (FIG. 6) to admit an upward beam of light of illuminate the bottom of each container passed over that aperture. As is seen in FIG. 6, the plate 56 is cut out along the line 162 to accommodate the light aperture for the device in box 160. In order to trigger the inspection function of the device in box 160, the starwheel 56 of said U.S. Pat. No. 3,191,773 is now replaced by a sensing device 163 (FIG. 3) which has a light 164 directed at a receiver 165 to set up a light beam across the gap 166 in the path of the sensing pins 144. The device 163 is identical to the device 145 previously described in connection with FIGS. 3 and 18. However, in this case the light beam of device 163 is adjusted so that it will not interfere with the actions of the devices 145 and 145A.

To illustrate more particularly, it is assumed that each sensing pin 144 represents the pitch or spacing of the grippers 45 about the periphery of the rotating plate 46. Normally, the location of the first light source 146 in device 145 will be on the pitch when a sensing pin 144 aligns opposite the first lamp 27. The light source 146A in device 145A will then be on the one-half pitch, or mid-way between two sensing pins, so that it will not be triggered by the sensing pin 144 until a pin 144 is aligned opposite lamp 31 and the pins 144 adjacent lamp 27 straddle the above referred to pin alignment for lamp 27. In such an arrangement of the devices 145 and 145A to create signals on the pitch and one-half pitch of the sensing pins 144, the device 163 for the inspection device 160 must be adjusted to create a signal at each one-quarter pitch of the sensing pins 144.

Figure 21:
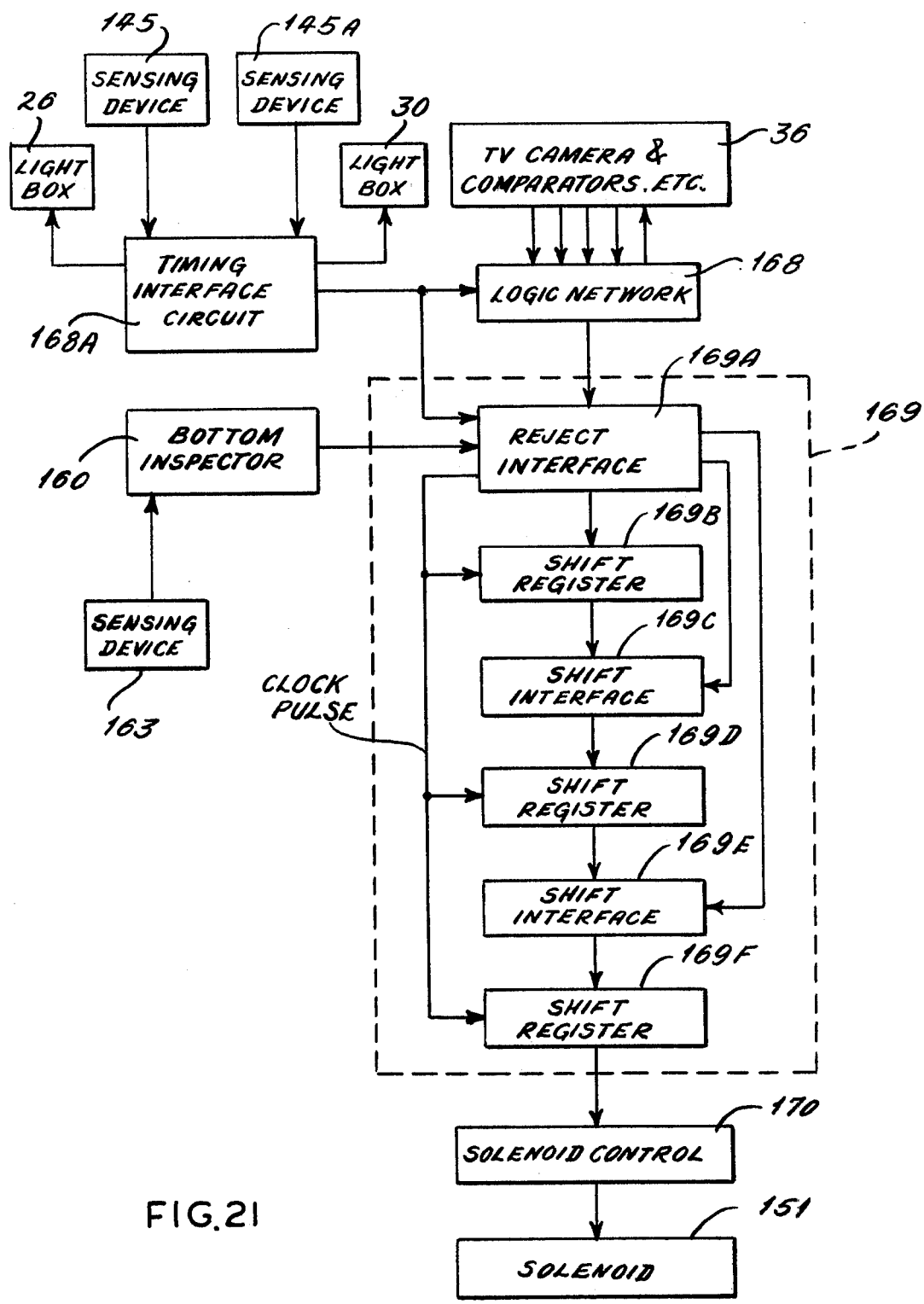
FIG. 21 is a block diagram of the container reject network for the present apparatus.

FIG. 21 showed the block diagram for the necessary circuits to process the reject signals produced by the TV camera 36 and the associated circuits due to the flaws existing on the side walls of the container. Logic network 168 will produce a signal only when the container under inspection by the camera is faulty. This reject signal will feed the reject delay network 169 and the reject delay network 169 is composed of circuits 169A to 169F which function in the following manner:

The reject signals from the logic network 168 and the bottom inspector 160 feed the reject interface circuit 169A. This circuit conditions and identifies the signals as three definite reject signals corresponding to the inspector 160, side inspection at box 26 and side inspection at box 30.

As shown in FIG. 3 where the sensing devices 145, 145A and 163 are located, and with respect to the diagram of FIG. 21, each container introduced to the apparatus passes under the inspection device 160 corresponding to device 163 and if found faulty produces a signal that is fed into the reject interface 169A of the reject delay network 169. Each container must also pass the side inspection box 26 where the sensing device 145 generates a signal which is sent through the timing interface circuit 168A to the box 26 where the circuit therein (not shown) causes the lamp 27 to generate a brilliant and short duration flash of light. The same events take place at box 30 when the signal from sensing device 145A indicates the presence of a container and causes the lamp 31 to generate a brilliant light flash. As noted before, the lamps 27 and 31 do not flash at the same time because the sensing devices are out of phase with the spacing of the sensing pins 144, and the same out-of-phase condition is necessary for sensing device 163. The timing of the light flashes is conditioned by the interface circuit 168A and fed into the logic network 168 and during a predetermined inspection period, if a container is seen by the TV camera 36 to be faulty, a signal is fed into the reject interface network 169A. The conditioned signals from the timing interface network 168A are also passed into the reject interface 169A. Reject pulse from 169A and corresponding to the inspector 160 feeds the shift register circuit 169B. This circuit is composed of a chain of shift registers designed to store and shift the signals synchronously with the container movement from one sensing pin 144 position to the next. For the sake of simplicity of container ejection at reject station, the timing pulses corresponding to any one of the stations can be used as the clock pulses for shift registers. In this disclosure, the timing pulses for station at box 26 is chosen to be the shift clock and the sequence of inspection would thus be box 26, box 30, and box 160 as shown in FIG. 1. The shifted reject pulse from register 169B feeds the shift interface circuit 169C which also accepts the reject signal from circuit 169A corresponding to box 26. The circuit 169C is designed to produce individual reject pulses for different containers inspected at stations 26 and 160 if found faulty, but produce only one reject pulse when the same container is found faulty by inspector 160 as well as the inspection at box 26. The signal from 169C is then fed to another chain of registers 169D. This circuit shifts the reject signals from boxes 26 and 160 until the faulty container arrives at box 30. At this station the same container is again inspected and if found faulty, another signal from circuit 169A corresponding to this station will be initiated and fed into the interface circuit 169E. Again, the circuit 169E has the ability to combine the reject signals for the same container at box 30 as well as reject signals for the same container at boxes 26 and 160 that by now have been stored and shifted to box 30 and produce only one signal for the container even though the same container has been found faulty at all three stations. After final inspection the reject pulse from 169E is fed to shift register 169F which shifts the pulses until the container arrives at the reject station defined by the device 150. At this station a pulse will be initiated by register 169F to activate solenoid control circuit 170 that in turn controls the action of the solenoid 151. The plunger on the solenoid will then be projected into the path of the gripper roller 139 to open the gripper jaw 135 and allow the container to fall on the reject plate 120.

Successful operation of the TV camera 36 for container inspection requires that the background lighting be directed towards the container in a manner to override the effects of the stray ambient lights. This is generally achieved by selecting a light source of sufficient intensity. However, when this light is directed towards the container, the TV camera 36 will see two distinct portions of light coming from the light boxes 26 or 30. A useful portion is transmitted through the container and highlights the surfaces of the container for the purpose of seeing the flaws against the background of the container. The second portion is the light which does not transmit through the bottle but emanates from the light box and arrives at the lens system in two parts. One part will arrive at the camera directly from the light box. The other part will arrive at the lens system after multiple reflections and refractions through the bottle. These two unwanted light parts having sufficient intensities will readily be accepted by the photo-sensitive element of the TV camera 36 as the "background" lighting if not eliminated, and will "overwhelm" the vidicon tube resulting in deterioration of relative photo-sensitivity of the vidicon for the useful light transmitting through the bottle. In order to eliminate these undesirable effects, a screen is used on each of the light boxes 26 and 30 with an opening contoured to the general shape of the container under inspection so that the light emanating from the opening will just envelop the whole body of the container. Such an aperture used on each light box is indicated at 29A in FIG. 3A.

Figure 22:
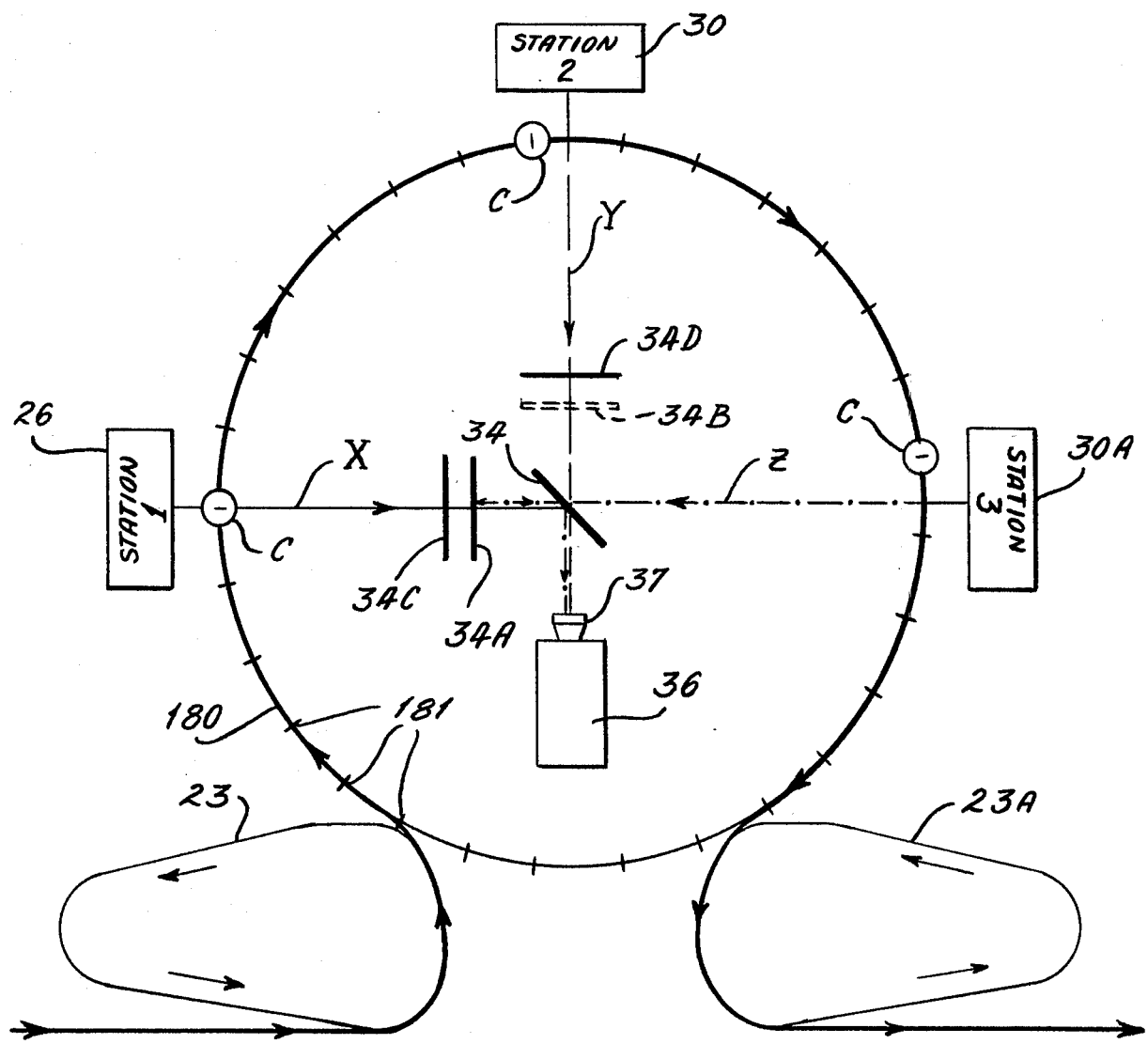
FIG. 22 is a schematic plan view of a modified arrangement in which by means of the light beam directing means the images of containers reaching the inspection stations can be sequentially viewed by the same sensing means.

A modification of the foregoing apparatus is shown in FIG. 22 which is a greatly simplified schematic plan view of the apparatus shown in FIG. 1, but arranged with a third inspection station 30A which structurally is similar to the inspection stations depicted by the boxes 26 and 30 heretofore described as containing a vertically elongated lamp positioned in front of a focussing reflector to direct a light beam through a diffusion plate toward the center of the circular travel of the ring plate 46 shown in FIG. 4. In the view of FIG. 22 the container feeding conveyor is schematically shown at 23 for the purpose of introducing the containers into the gripping means (not shown) for the container necks. The line of travel of the gripping means is depicted at 180, and the short radial lines 181 indicate the positions for the array of gripping means of the character shown at 45 in FIGS. 15, 16 and 17. The gripping means 45 suspend the containers and cause them to travel along the path 180 through the respective stations 1, 2 and 3, and the containers are discharged from the apparatus at the conveyor 23A. It is not believed important to indicate in FIG. 22 the location of the reject conveyor 23B, as that is clearly shown in FIG. 1 to be just beyond the location of station 3.

The arrangement for directing the illuminated images of the containers developed at the respective inspection stations is modified, as shown in FIG. 22, so that the single television camera 36 will be able to scan each of the container images as they are produced. For example, when a container C passes in front of inspection station 1 the illuminated image thereof travels along the beam axis line X, traverses a suitable filter 34C and a beam splitter device 34A. The latter device is positioned so as to be perpendicular to the image axis X and not to divert the illuminated image which passes to the master beam splitter 34 to be directed through the camera lens assembly 37 and into the camera 36.

While the container C at station 1 is producing an illuminated image, a different container C is approaching inspection station 2 one-quarter pitch away, but is not yet in position to have an image generated at station 2. Similarly a different container C approaching inspection station 3 is located one-half pitch away such that it will not generate and image until the container image at station 2 has been generated. When the container C reaches inspection station 2 its illuminated image will travel along the beam axis Y and pass through a suitable filter 34D before encountering the master beam splitter 34 where the image will pass through and be picked up by the camera lens assembly 37. The next container C reaching station 3 will generate an illuminated image thereof which travels along beam axis Z, and will travel through the master beam splitter 34, but because the beam splitter device 34A is set perpendicularly to the beam axis Z the reflected portion of the image from the device 34A will return to the master splitter 34 and be directed into the camera 36 through the lens assembly 37.

It is noted in FIG. 22 that the splitter device 34A may also be located at position 34B shown in dotted outline where the latter device is set perpendicularly to the beam axis Y from station 2. In either case, suitable light components from the container image will arrive in line with each other at the lens assembly 37 so that the camera 36 will be able to analyze the individual images coming from each station in a sequential manner. Under this condition, the speed of inspection by the camera 36 will be 4 times the speed of travel of the containers along the path 180. It is understood of course that suitable photosensitive elements should be utilized for the camera 36 so that inspection speed can be properly correlated to obtain maximum speed of travel of the containers around the path 180. It is also pointed out that in order to obtain uniform image intensities in the lens assembly 37, suitable filters 34C and 34D will be necessary for the light beam paths from stations 1 and 2 to compensate for the light attenuation caused by the addition of the splitter device 34A (or 34B) for viewing the containers as they pass through station 3. As shown in FIG. 22 inspection stations 1 and 2 are separated by 90° of arc and stations 2 and 3 are also separated by 90° of arc. For angles of separation other than 90°, variations from the above arrangement will have to be applied.

The foregoing description has set forth the details of a presently preferred embodiment of apparatus to perform inspection of the entire body of containers without specifically rotating the containers in front of the inspection light sources. The apparatus is arranged to move containers at speeds up to the responsiveness of the TV camera type photoelectronic scanner 36 because that scanner is required to look at containers passing each of the inspection lights in boxes 26, 30 and 30A in sequence. While the inspection performed by the components in box 160 does not employ a device like the scanner 36, all of the inspection steps performed must be capable of creating a reject signal which by the suitable control circuits of FIG. 21 operates the reject device 150 at the proper time to release a rejected container to the reject receiving conveyor 23B.

What is claimed is:

1. A method of inspecting transparent containers for foreign objects, said method comprising the steps of gripping and creating a flow of containers in predetermined spaced relation along a curved path having a predetermined radius of curvature, directing the container flow through inspection stations that are spaced apart, causing the motion of the containers through the inspection stations to initiate the inspection steps which at certain stations energizes a source of illumination for passing a beam of light through the containers, directing the emerging lighted container images in directions which are coincident with the predetermined radius of curvature and coinciding at a common place of intersection, directing photosensitive scanning means toward said place of intersection of the lighted images to receive and scan the successive illuminated images for changes in the intensity of the illumination, and turning the gripped containers between inspection stations to align a different side of the containers with the sources of illumination and thereby to present a different illuminated image to the photosensitive means, and controlling the time of energization of the source of illumination so that one lighted image of a container at a time is scanned.

2. A method of inspecting elongated containers for foreign matter and rejecting unacceptable containers, said method including: gripping the containers by the necks and causing the containers to rotate about the axis of elongation while moving them along a predetermined path with the bottoms of the containers suspended at a first elevation; inspecting the containers from the sides during movement along said path; releasing rejected containers from said path at a predetermined location beyond said inspection means to fall free onto a support surface at a second elevation below said first elevation of the container bottom to catch and support the containers by the bottoms; guiding the rejected containers out of said predetermined path, whereby the flow of acceptable containers is cleared of rejected containers, and stabilizing the positions thereof as the containers move clear of acceptable containers.

3. A method of inspecting and moving containers through a plurality of spaced apart inspection stations and rejecting unacceptable containers from those that are acceptable, said method comprising: defining a predetermined path of travel for the containers in spaced apart relation and from a container inlet into that path and through the inspection stations and a container reject zone to a container outlet; gripping the containers by the necks and suspending them in spaced relation with the bottoms at a first elevation and free of support; turning the gripped containers during movement between the spaced inspection stations; inspecting the containers at the spaced inspection stations where a different side of each container is non-rotatively presented for inspection; releasing the grip on a container found to be unacceptable; and releasing the unacceptable containers to drop to positions at a second elevation out of the path of travel for acceptable containers, to be captured and stabilized as they drop to the second elevation from the predetermined path and at a rate commensurate with the passage of acceptable containers.

4. A method of inspecting open mouth frangible type containers for the presence of foreign matter and rejecting those containers carrying objectionable foreign matter, the steps of establishing a path of travel for all containers through at least two spaced apart inspection stations, feeding the containers into the path of travel at an inlet, gripping the containers at the inlet to the path of travel so as to suspend them by the neck adjacent the open mouth so as to leave the sides unobstructed during travel in said path, turning the containers during the travel along the path between the inspection stations to non-rotatively present a different side of each container for inspection at each inspection station, directing a light beam through the side of each container at each inspection station, sensing the level of illumination of the container images, continuing the travel of the containers to an outlet beyond the last of the two inspection stations, releasing the grip on containers carrying objectionable foreign matter which has altered the level of illumination during sensing of the light level in advance of the outlet, allowing the released containers to fall free of the path of travel of other containers traveling to the outlet, and guiding the released containers into a path of travel diverging from the established path of travel.

5. Apparatus for inspection of transparent containers comprising a stationary cam means, a rotating head having circumferentially spaced pockets therein, means carried by said pockets and operated by moving relative to said cam means to grip and hold containers suspended from said pockets during rotation of said head, means to feed containers into said spaced pockets and to receive inspected containers from said spaced pockets, a plurality of inspection stations spaced apart along the circumference of said rotating head, each station having a light source directing a beam toward the center of rotation of said head, a light sensing device disposed adjacent said center of rotation, means responsive to rotation of said head and connected to the light sources in said stations to energize the light sources in said stations in sequence, and means carried by said container holding means to engage said cam means to rotationally orient the holding means relative to said head and thereby turn the containers in said pockets such that a different side of each container is presented to each of said stations for illumination and viewing by said light sensing device.

6. The apparatus set forth in claim 5 wherein said pockets in said head are spaced apart a distance such that said pockets align the containers with one inspection station at a time whereby the light sources are energized one at a time.

7. The apparatus set forth in claim 5 wherein said stations are spaced apart along the arc of said rotating head, and beam directing means positioned between said stations and said light sensing device and to receive each light beam sequentially.

8. Apparatus to inspect transparent containers for foreign matter comprising means defining a curved path having a predetermined radius of curvature and adapted to move the containers along a predetermined portion of said curved path in spaced relation and past inspection stations, container illumination means at each said inspection station in position to illuminate each container moved along said path and produce an image of the illuminated portion of the containers, said container images being directed along the radius of curvature and coinciding at a common place of intersection, scanner means common to said inspection stations and positioned adjacent said common place of intersection to receive in sequence each container illuminated image and sense significant changes in the intensity of the illumination, sensing means carried by said container moving means and spaced apart so as to be related one with each container moved along said path, electrical sensing devices connected to said illumination means to produce an illuminated image of the container related with each of said sensing means, means beyond said inspection stations to effect the rejection of a container determined by said scanner means to carry objectionable foreign matter, and other circuit means electrically relating said scanner means, electrical sensing devices and said container rejection means to operate said rejection means when a container to be rejected arrives at said rejection means.

9. The apparatus of claim 8 wherein said container moving means is a rotating head having container holding means thereon to grip the container necks, there being as many holding means as sensing means.

10. The apparatus of claim 8 wherein said electrical sensing devices are located such that the passage of a sensing means will generate a signal pulse to result in sequential illumination of the containers.

11. The apparatus of claim 8 wherein said container moving means is a rotating head, said inspection stations are spaced along the periphery of the rotary path of movement of said rotating head, said container illumination means at each station directs the illuminated image inwardly along the radius of curvature, means at said common place of intersection to direct the images toward a common path of travel, and said scanner means receives the illuminated images from said common path of travel.

12. The apparatus of claim 11 wherein said means at said common path of travel is beam splitter means, and said electrical sensing devices are located such that the passage of a sensing means will generate a signal pulse to result in sequential illumination of the containers so that the scanner means receives the container images one at a time.

13. Apparatus for inspecting transparent containers comprising stationary cam means, a rotating head having circumferentially spaced pockets therein, means operated by said cam means to hold containers in said pockets during rotation of said head, said holding means carried by said head comprise grippers operated by said cam means to turn said container holding means, means to feed containers into said spaced pockets and to receive inspected containers from said spaced pockets, a plurality of inspection stations spaced apart along the circumference of said rotating head, each station having a light source directing a beam toward the center of rotation of said head, a light sensing device disposed adjacent said center of rotation, means responsive to rotation of said head and connected to the light sources in said stations to energize the light sources in said stations in sequence, and means carried by said head and said container holding means to rotationally orient the containers in said stations such that container images directed out of said stations are each different to present a different side of the container to said light sensing device.

* * * * *